United States Patent [19]

Womack

[11] Patent Number: 5,730,988
[45] Date of Patent: Mar. 24, 1998

[54] NUTRITIONAL SUPPLEMENTS FOR IMPROVING GLUCOSE METABOLISM

[75] Inventor: Rick W. Womack, Houston, Tex.

[73] Assignee: Lynntech, Inc., College Station, Tex.

[21] Appl. No.: 822,483

[22] Filed: Mar. 24, 1997

Related U.S. Application Data

[63] Continuation-in-part of Ser. No. 425,582, Apr. 20, 1995, Pat. No. 5,614,224.

[51] Int. Cl.$^6$ .................. A61K 31/205; A61K 31/38; A61K 33/24; A61K 35/78

[52] U.S. Cl. .................. 424/195.1; 424/617; 424/646; 514/440; 514/556; 426/74

[58] Field of Search .................. 424/195.1, 617, 424/646; 514/440; 426/74

[56] References Cited

U.S. PATENT DOCUMENTS

| | | | |
|---|---|---|---|
| 5,087,623 | 2/1992 | Boynton et al. | 514/188 |
| 5,087,624 | 2/1992 | Boynton et al. | 514/188 |
| 5,164,384 | 11/1992 | Paul | 514/188 |
| 5,175,156 | 12/1992 | Boynton et al. | 514/188 |
| 5,270,297 | 12/1993 | Paul et al. | 514/23 |
| 5,292,538 | 3/1994 | Paul et al. | 426/74 |
| 5,614,224 | 3/1997 | Womack | 424/646 |

OTHER PUBLICATIONS

Jeejeebhoy et al., J. Clin. Investig. (57) Jan., 1976, 125–136.

*Primary Examiner*—Phyllis G. Spivack
*Attorney, Agent, or Firm*—Patterson & Streets L.L.P.

[57] ABSTRACT

The invention provides nutritional supplements and methods for administering nutritional supplements that improve glucose metabolism, particularly for persons with diabetes. A first nutritional supplement, or "Phase I" supplement, comprises a source of vanadate and a source of chromium. A second nutritional supplement, or "Phase II" supplement, comprises Gymnema sylvestre and lipoic acid. The nutritional supplements are alternated to prevent accumulation of the nutrients in the body and also to overcome desensitization that can occur over long periods of continuous use. While the nutritional supplements may be alternated at almost any frequency and taken over almost any duration, it is preferred that each Phase be taken for between about 2 and about 6 months, most preferably about 3 months or about 90 days, before alternating back to the other Phase.

24 Claims, No Drawings

NUTRITIONAL SUPPLEMENTS FOR IMPROVING GLUCOSE METABOLISM

This is a continuation-in-part of application Ser. No. 08/425,582 filed on April 20, 1995, now U.S. Pat. No. 5,614,224.

FIELD OF THE INVENTION

The present invention relates to nutritional supplements and methods of using them. More particularly, the present invention relates to a nutritional supplements which assist in the metabolism of glucose.

BACKGROUND OF THE DISCLOSURE

Diabetes mellitus is caused in almost all instances by diminished rates of secretion of insulin by the beta cells of the islets of Langerhans in the pancreas. Diabetes is usually divided into two different types: juvenile diabetes that usually, but not always, begins in early life, and maturity-onset diabetes that usually, but not always, begins in later life and mainly in obese persons.

Maturity-onset type of diabetes is likely to occur in those with a family history of diabetes and is characterized by blurred vision, itching, unusual thirst, drowsiness, obesity, fatigue, skin infections, slow healing, and tingling or numbness in the feet. Onset of symptoms is usually later in life. The maturity-onset type of diabetes seems to result from degeneration or suppression of the beta cells as a result of more rapid aging in susceptible persons than in others. Obesity predisposes an individual to this type of diabetes, probably for two different reasons. First the beta cells of the islets of Langerhans in an obese person become less responsive to stimulation by increased blood glucose levels. Therefore, the surge of insulin secretion following a meal is less marked in obese persons. Second, obesity also greatly decreases the number of insulin receptors in the insulin target cells throughout the body. For these reasons, increased quantities of insulin are required to have the same metabolic effects in obese persons as in persons who are not obese.

Most of the pathology of diabetes mellitus can be attributed to one of three major effects of insulin lack. First, low levels of insulin cause a decrease in the utilization of glucose by the body cells with a resultant increase in blood glucose concentration to as high as 300 to 122 mg/dl. Second, insulin lack causes a markedly increased mobilization of fats from the fat storage areas, resulting in abnormal fat metabolism as well as deposition of lipids in vascular walls to cause atherosclerosis. Third, insulin lack can result in a depletion of protein in the tissues of the body.

Typical treatment of diabetes mellitus, including full-blown cases of maturity-onset diabetes, involves administering enough insulin so that the patient will have as nearly normal carbohydrate, fat, and protein metabolism as possible. Optimal therapy can prevent most acute effects of diabetes and greatly delay the chronic effects as well.

Insulin is available in several different forms. Regular insulin has a duration of action lasting from 3 to 8 hours, whereas other forms of insulin are absorbed slowly from the injection site and therefore have effects that last as long as 10 to 48 hours. Ordinarily, the severely diabetic patient is given a single dose of a longer-acting insulin each day to increase overall carbohydrate metabolism throughout the day. Then additional quantities of regular insulin are given at those times of the day when the flood glucose level tends to rise too high, such as at meal times. Thus, each patient is established on an individualized pattern of treatment.

Frequently, following a special diet can control maturity-onset diabetes sufficiently so that insulin is no longer required. It is recommended that an individual with maturity-onset diabetes follow a high-carbohydrate, high-fiber diet to reduce the need for insulin and lower the fat levels in the blood.

An estimated 5.5 million Americans are being treated for diabetes. In addition, studies estimate that there are 5 million adults with undetected maturity-onset diabetes and another 20 million having impaired glucose tolerance that may lead to full-blown diabetes. The National Institutes of Health report that undiagnosed diabetes is the reason behind millions losing their vision. Diabetes is the third leading cause of death in the United States.

Therefore, there is a need for a composition and method for enhancing glucose metabolism in individuals with maturity-onset diabetes and thereby reduce or prevent the necessity of using insulin. It would be desirable if this composition and method were convenient to administer and cost less than insulin so that it could be easily afforded by individuals with low incomes who have no insurance coverage. It would also be desirable if such a composition could be purchased over the counter, thereby making it more widely available to individuals at high risk of maturity-onset diabetes.

SUMMARY OF THE INVENTION

The present invention provides a nutritional system for improving glucose metabolism, comprising a first supplement comprising a source of vanadate and a source of chromium and a second supplement comprising Gymnema sylvestre and lipoic acid. Gymnema sylvestre is provided as an extract from Gymnema sylvestre leaves. The preferred source of vanadate is vanadyl sulfate and the preferred source of chromium is selected from the group consisting of chromium picolinate, chromium glucose tolerance factor, and mixtures thereof. The source of chromium may comprise both chromium picolinate and chromium glucose tolerance factor. It may be desirable for the first supplement to further comprises L-carnitine.

Another aspect of the invention provides a nutritional system for improving glucose metabolism, comprising a first supplement comprising a source of vanadate and a second supplement comprising a component selected from the group consisting of Gymnema sylvestre, lipoic acid and combinations thereof, wherein the second supplement is substantially free from vanadate. The first supplement preferably further comprises a source of chromium.

Yet another aspect of the invention provides a method of administering a nutritional supplements. The method comprises the steps of administering a daily dosage of a first nutritional supplement over a first time period and administering a daily dosage of a second nutritional supplement over a second time period following the first time period. These steps may be repeated as desired. In one embodiment, the first nutritional supplement comprises a source of vanadate and a source of chromium, and the second nutritional supplement comprises Gymnema sylvestre and lipoic acid. In an alternative embodiment, the first nutritional supplement comprises Gymnema sylvestre and lipoic acid, and the second nutritional supplement comprises a source of vanadate and a source of chromium. The first and second time periods may be the same or different, preferably between about 2 and about 6 months, most preferably about 3 months or about 90 days.

DETAILED DESCRIPTION OF A PREFERRED EMBODIMENT

The present invention provides a nutritional supplement that enhances glucose metabolism. While the supplement may be used by individuals with no apparent symptoms of diabetes, the supplement is ideal for use by individuals with maturity-onset diabetes or juvenile diabetes to prevent, reduce or eliminate the necessity of using insulin. The supplement contains ingredients which work together to enhance the effect of insulin on the regulation of glucose concentration in the blood by facilitating or assisting metabolism of glucose in the cells of the body.

In one aspect of the invention, a nutritional supplement is provided which comprises a source of vanadate, such as vanadyl sulfate, and a source of chromium, such as chromium picolinate. The nutritional supplement produces insulin-like effects that prevent, reduce or eliminate the need to administer insulin. It is preferred that the supplement be taken throughout the day in order to make the vanadate and chromium available to the cells when needed. It is particularly preferred that the daily dosage be taken in approximately equal amounts with breakfast, lunch and dinner in order for the nutrients to assist in glucose metabolism following mealtime when they are needed the most. Optionally, the nutritional supplement may further comprise L-carnitine.

In another aspect of the invention, an alternative nutritional supplement is provided with comprises a source of gymnema sylvestre and a source of lipoic acid. This alternative nutritional supplement also produces insulin-like effects the prevent, reduce or eliminate the need to administer insulin. It is preferred that the supplement be taken throughout the day in order to make the vanadate and chromium available to the cells when needed. It is particularly preferred that the daily dosage be taken in approximately equal amounts with breakfast, lunch and dinner in order for the nutrients to assist in glucose metabolism following mealtime when they are needed the most.

In yet another aspect of the invention, a plurality of nutritional supplements and a nutritional program are provided. The plurality of nutritional supplements comprise a "Phase I" supplement comprising a source of vanadate and a source of chromium and a "Phase II" supplement comprising a source of gymnema sylvestre and a source of lipoic acid. The plurality of nutritional supplements are alternated to prevent accumulation of the nutrients in the body and also to overcome desensitization that can occur after a nutrient is taken over a period of time. While the nutritional supplements may be alternated at almost any frequency and taken over almost any duration, it is preferred that each Phase be taken for between about 2 and about 6 months, most preferably between about 2 and about 3 months, before alternating back to the other Phase.

In a further aspect of the invention, the nutritional supplement may optionally include other certain vitamins, minerals, amino acids, enzymes and/or herbs. These additional ingredients may be included in a common pill along with the vanadyl sulfate, chromium picolinate and L-carnitine or may be taken as a separate pill, preferably taken more or less simultaneously.

Nutritional supplements according to the present invention are not intended to eliminate the need for an individual to follow a program of appropriate diet and exercise, nor does it eliminate the need for insulin in all cases. Rather, the supplements of the present invention improve glucose metabolism by enhancing the effects of natural or administered levels of insulin and an appropriate diet and exercise program.

A nutritional supplement containing effective amounts of metabolically available forms of vanadate and chromium will improve glucose metabolism, particularly in individuals with maturity-onset diabetes. Vanadate and chromium perform different insulin-like functions which, when administered in appropriate ratios and forms, enhance glucose metabolism in substantially the same way as insulin itself.

As discussed above, insulin performs at least two important functions. First, insulin improves the utilization of glucose by the body cells which in turn controls blood glucose concentrations from getting too high. Second, insulin transports fatty acids to fat cells for storage, thereby reducing the mobilization of fats from fat storage areas which can result in abnormal fat metabolism as well as deposition of lipids in vascular walls to cause atherosclerosis.

The first function of insulin mentioned above, that of improving the utilization of glucose, is enhanced by the combination of vanadate and chromium. Vanadate ions, like insulin, stimulate glucose transport, activate glycogen synthase, increase glycogen syntheses in fat cells, and stimulate carbohydrate uptake in the liver. Glycogen synthase is an enzyme which causes the conversion of glucose into glycogen. Glycogen itself is a polysaccharide which is the chief carbohydrate storage material in humans. It has been found that maximum glycogen synthase activation produced by vanadate is indistinguishable from that of insulin. Evidence that strongly suggests a common mechanism of action for insulin and vanadate includes the following findings: (1) with maximum insulin, additional quantities of vanadate are without effect; (2) with sub maximal insulin, additional quantities of vanadate increase both the glycogen synthase activation state and 2-deoxyglucose transport to the level obtained with maximum insulin; (3) insulin and vanadate counteract the activating effect of adrenaline on glycogen phosphorylase in a similar manner; adrenaline partially reverses vanadate and insulin activate glycogen synthase within similar time frames. Thus, the presence of invivo vanadate can lead to improved glucose metabolism and enhance the effects of natural or administered levels of insulin.

The preferred source of vanadate is vanadyl sulfate. Once ingested, vanadyl sulfate typically forms vanadate which is a salt of vanadic acid. While doses as low as 10 mg of vanadyl sulfate may provide some enhancement of glucose metabolism, the preferred dosage of vanadyl sulfate for an individual with diabetes weighing from about 150 pounds to about 250 pounds is in the range between about 30 mg and 150 mg per day. The most preferred dosage of vanadyl sulfate is about 60 mg per day. Whereas vanadyl sulfate has been previously included in certain dietary supplements, dosages ranging between 1 mcg and 1,000 mcg (1 mg) are inadequate to provide significant insulin-like effects.

Chromium, like vanadyl sulfate, possesses properties which both mimic and enhance the effects of insulin. Chromium enhances the effects of insulin by indirectly assisting amino acid uptake by muscles, stimulates protein synthesis and retards the rate of protein breakdown. Many clinical studies with supplemental chromium have shown only modest improvements in glucose tolerance due to poor absorption of nutritional (trivalent) chromium. In this respect, trivalent chromium has a strongly positive charge that impedes its movement across cell membranes. Due to the presence of competing ions such as copper, iron, manganese and zinc in the human body, adequate absorption of chromium occurs only when the metal is associated with a natural chelating agent, such as picolinic acid. Because of its unique structure, picolinic acid has a strong affinity for transitional metals such as zinc, manganese, and chromium.

In this respect, it binds tightly to these metals thereby neutralizing their positive charges and expediting their movement across cell membranes.

It is preferred that chromium be provided in a biologically active form of chromium, particularly chromium picolinate or chromium glucose tolerance factor. In chromium picolinate, the picolinic acid serves as an effective metal chelator that improves the utilization and uptake of the chromium and plays an important physiological roll in trace mineral absorption. Chromium is believed to be the active factor while the picolinic acid serves as the chelator to improve bioavailability. Animal studies have shown chromium picolinate to be absorbed and retained five to ten times better than other forms of chromium and have also found it to be remarkable safe. The preferred dosage of chromium picolinate for an individual with diabetes weighing from about 150 pounds to about 250 pounds is in the range between about 150 and about 600 mcg per day, with about 300 mcg per day being most preferred. The preferred dosage of chromium glucose tolerance factor is between about 50 and about 400 mcg per day, with about 100 mcg per day being most preferred. While the supplement may include only one form of chromium, it is preferred that the supplement include both forms in their preferred doses given above.

The second function of insulin mentioned above, that of transporting fatty acids to fat cells for storage, may be enhanced by L-carnitine. By preventing fatty build-up, this amino acid aids in weight loss, decreases the risk of heart disease, and improves athletic ability. Carnitine can be manufactured in the body if sufficient amounts of lysine, B1, B6 and iron are available. However, vegetarians are more likely to be deficient in carnitine due to a diet that is low in lysine. The preferred dosage of L-carnitine for an individual with diabetes weighing from about 150 to about 250 pounds is in the range between about 100 mg and about 1,000 mg per day. The most preferred dosage of L-carnitine is about 150 mg.

Because L-carnitine can be manufactured in the body, it is possible to complement the L-carnitine with sufficient amounts of lysine, vitamin B1, vitamin B6 and iron to facilitate production of L-carnitine. Therefore, while lysine, vitamin B1, vitamin B6 and iron are not essential to the function of the present invention, it is preferred that the supplement include between about 5 and about 10 mg per day of both vitamins B1 and B6, and between about 10 mg and about 25 mg of iron. It is most preferred that vitamins B1 and B6 be supplied by a dose of between about 30 mg and about 70 mg of a B-complex.

Two water soluble extracts, GS3 and GS4, obtained from the leaves of Gymnema sylvestre, a woody climber growing in the tropical forests of central and southern India, may be used to bring about blood glucose homeostasis through increased serum insulin levels. It is believed that Gymnema sylvestre appears to enhance endogenous insulin, possibly by regeneration/revitalization of residual beta cells in the endocrine pancreas that are responsible for insulin production. Daily supplementation with Gymnema sylvestre has been shown to cause a significant reduction in blood glucose, glycosylated hemoglobin and glycosylated plasma proteins, thereby allowing conventional drug dosages to be decreased. Both juvenile and adult onset diabetes appear to respond to the action of Gymnema sylvestre.

Lipoic acid has been found to exhibit antioxidant properties and metabolic enhancement which facilitates regeneration of damaged nerves. Lipoic acid also appears to reduce the degree of glycation, or reaction, of proteins caused by excess blood sugar, which is common in diabetics. It is generally recognized that many of the metabolic complications that occur in diabetics are a result of persistent elevation of blood sugar, which then attaches to the blood proteins. Lipoic acid substantially reduces glycation, increases insulin sensitivity, and may lower flood sugar levels.

The present invention provides a first nutritional supplement for diabetics which combines vanadyl sulfate and chromium picolinate. It is also preferred that the first nutritional supplement include L-carnitine. The present invention also provides a second nutritional supplement for diabetics which combines Gymnema sylvestre and lipoic acid.

The supplements of the present invention are formulated to produce insulin-like effects that prevent, reduce or eliminate the need to administer insulin. It is preferred that either supplement be taken throughout the day to be available to the cells as needed. It is particularly preferred that the daily dosage be taken in approximately equal amounts with breakfast, lunch and dinner. Each of the supplements of the present invention provide nutrients to assist in glucose metabolism following mealtime when they are needed the most.

The present invention further provides a nutritional system and method for diabetics which avoids desensitization that can occur after taking the same supplement continuously for a prolonged period of time. The nutritional system comprises both the first and second nutritional supplements, described above, maintained in separate capsules, preferably even in separate bottles. The nutritional system is administered by taking a daily dosage of either the first or second nutritional supplements for a period of months, then switching to the other nutritional supplement for a period of months. The period of months for administering the first and second nutritional supplements may be the same or different lengths of time. However, the preferred period of months is between about 2 and about 6 months, with the even more preferred period of months being between about 2 and about 4 months. The most preferred period of months is about 3 months or 90 days.

It is noted that the first and second nutritional supplements could be combined in a single pill, alternated between meals, alternated daily or alternated at any other frequency, and still be effective for reducing the effects of insulin lack. However, the cells of the body would eventually become desensitized to such supplements or methods of administering the supplements because of the substantially continuous presence of the nutrients. The present invention is most effective over extended period of time by alternating supplements after a period of months. It is important to understand that the period of months allows sufficient time for the body to clear itself of trace amounts of the nutrients and to avoid desensitization. Accordingly, as other nutrients are found to have beneficial effects on glucose metabolism, it may be desirable to provide additional nutritional supplements that can be administered in a rotation. In this manner, the period of months between successive use of the same supplement could be extended.

It may be desirable that the nutritional supplements include other certain vitamins, minerals, amino acids, enzymes and/or herbs. These additional ingredients may be included in a single pill along with the vanadyl sulfate, chromium picolinate and L-carnitine or may be taken as a separate pill taken more or less simultaneously.

Vitamins that are particularly beneficial to the metabolism of glucose are the B-complex vitamins and vitamin A. Even where the supplement includes L-carnitine, it is preferred that the supplement include between about 5 and about 10 mg per day of both vitamins B1 and B6, and between about 40 mg and about 60 mg per day of niacinamide (vitamin B3). It is most preferred that the supplement include a dose of between about 30 mg and about 70 mg per day of B-complex vitamins where the amounts of vitamins B1, B3 and B6 included therein are about 6 mg, 50 mg and 6 mg, respectively.

Vitamin A is necessary to the utilization of protein. It may be taken as beta-carotene, which is converted to vitamin A in the liver, or as the vitamin itself. The preferred dose of vitamin A is between about 10,000 IU and about 20,000 IU per day, with the most preferred dose being about 15,000 IU per day.

Minerals are also important in the metabolism of glucose and may be ingested from food or included in a supplement. In order to be certain that sufficient amounts of the most important minerals are available, it is preferred that the supplement also include magnesium, potassium, calcium, copper, selenium, and zinc. The preferred daily doses of these minerals is about 380 mg magnesium, about 114 mg potassium, about 760 mg calcium, about 2 mg copper, about 80 mcg selenium, and about 50 mg zinc. It should be recognized that the amounts of these minerals can vary widely within the scope of the present invention. L-glutamine is an important amino acid in curbing fatigue and the craving for sugar. The preferred dose of L-glutamine is between about 100 mg and about 500 mg per day, with about 300 mg per day begin most preferred.

Many different enzymes may be incorporated into the supplement, in accordance with the invention, to assist in the digestion of food. The preferred enzymes include pancreatin, amylase, papain, lipase and betaine.

Pancreatin is an enzyme derived from the secretions of an animal pancreas. It is preferred that the supplement include pancreatin in doses ranging between about 50 and about 150 mg per day. It is most preferred that the supplement include about 100 mg pancreatin per day.

Amylase is an effective digestive enzyme secreted in high concentrations in the human body. Amylase is found in saliva and works to break down carbohydrates. It is preferred that the supplement include amylase in doses ranging between about 50 and about 150 mg per day. It is most preferred that the supplement include about 100 mg amylase per day.

Papain is a proteolytic enzyme that works exclusively to break down proteins. It is preferred that the supplement include papain in doses ranging between about 25 mg and about 70 mg per day each. It is most preferred that the supplement include about 45 mg per day of papain.

Lipase is an enzyme that aids in the digestion of fat. It is preferred that the supplement include lipase in doses ranging between about 80 mg and about 230 mg per day each. It is most preferred that the supplement include about 150 mg lipase per day.

Betaine, a preferred form of hydrochloric acid (HCl), aids in the digestion of tough foods, such as fibrous meats, vegetables, and poultry. It is also preferred that the supplement include between about 100 mg and 200 mg per day of betaine, with about 150 mg per day being most preferred.

Herbs beneficial against the causes of symptoms of diabetes, including high blood pressure, may also be incorporated into the supplement without departing from the scope of the invention. These herbs include, but are not limited to, ginseng, huckleberry, evening primrose oil, garlic, gotu kola, juniper berries, and suma. The preferred herbs are ginseng and huckleberry. The preferred dose of ginseng is between about 150 mg and about 350 mg per day, with about 275 mg per day being most preferred. The preferred dose of huckleberry is between about 100 mg and about 200 mg per day, with about 150 mg per day being most preferred.

Guar gum is a water soluble fiber that has been shown to lower blood glucose levels, aid in lowering cholesterol levels, and curb the appetite. Guar gum must be taken as a liquid as should not be included in any pills, capsules, tablets or other solid forms. However, the nutritional supplement of the present invention could be prepared in the form of a liquid drink which could include guar gum.

The supplements of the present invention can be manufactured in accordance with procedures known in the art. While the supplement may be formed into a pill with starch or a liquid drink, it is generally preferred that the supplement be prepared in a capsule.

EXAMPLE 1

Two nutritional supplements, Phase I and Phase II, were prepared according to the following daily dosages:

| Phase I | |
|---|---|
| Vanadyl Sulfate | 60 mg |
| Chromium (Picolinate) | 300 mcg |
| Chromium (Glucose Tolerance Factor) | 100 mcg |
| L-Carnitine | 150 mg |
| L-Glutamine | 300 mg |
| Magnesium | 380 mg |
| Potassium | 114 mg |
| Calcium | 760 mg |
| Copper | 2 mg |
| Vitamin A | 15,000 IU |
| Niacinamide (B-3) | 50 mg |
| Vitamin (B-1) | 6 mg |
| Vitamin (B-6) | 6 mg |
| Selenium | 80 mcg |
| Zinc | 50 mg |
| Pancreatin | 100 mg |
| Papain | 75 mg |
| Amylase | 100 mg |
| Betaine (HCL) | 75 mg |
| Lipase | 150 mg |
| Huckleberry | 150 mg |
| Ginseng | 275 mg |
| Phase II | |
| Gymnema sylvestre (extract) | 750 mg |
| Lipoic acid | 100 mg |
| Cat's claw | 500 mg |
| Pullunan | 350 mg |
| L-Methionine | 200 mg |
| Pancreatin | 100 mg |
| Lipase | 100 mg |
| Amylase | 100 mg |
| Dandelion root | 300 mg |
| Folic Acid | 400 mcg |
| Copper (chelated) | 2 mg |
| Iodine | 150 mcg |
| Manganese (chelated) | 7.5 mg |
| Selenium (chelated) | 80 mcg |
| Zinc (chelated) | 50 mg |
| Vitamin B-1 | 6 mg |
| Niacinamide (B-3) | 50 mg |
| Vitamin B-6 | 6 mg |

The daily dosages of both the Phase I supplement or the Phase II supplement were divided into six (6) capsules. Two of these six capsules were taken along with breakfast, lunch and dinner each day. Phase I was administered for a period of three months, then Phase II was administered for a period of three months. This pattern of alternating between Phases I and II was repeated to provide continuous benefits to diabetics while avoiding desensitization that can occur from continuous use of a single supplement formulation.

While much of the foregoing disclosure has focused on insulin lack, diabetes can also occur in individuals whose pancreas is producing plenty of insulin but the cells of the body are insulin resistant. Vanadyl sulfate can increase the response that a cell has to insulin by activating the insulin receptor sites on the surface of the cell and within the cell. Furthermore, this activation of insulin receptors may be permanent.

The nutritional supplement of the present invention may be used not only as a treatment for poor glucose metabolism or diabetes, but also for prevention of diabetes by giving the metabolism a boost before full-blown diabetes develops. In fact, because the activation of insulin receptors and other effects may be permanent, the supplement could be considered to be a cure for diabetes in some individuals and circumstances.

It will be understood that certain combinations and sub combinations of the invention are of utility and may be employed without reference to other features in sub combinations. This is contemplated by and is within the scope of the present invention. As many possible embodiments may be made of this invention without departing from the spirit and scope thereof, it is to be understood that all matters hereinabove set forth or shown in the accompanying drawing are to be interpreted as illustrative and not in a limiting sense.

While the foregoing is directed to the preferred embodiment, the scope thereof is determined by the claims which follow:

What is claimed is:

1. A nutritional system, comprising:
    a first supplement comprising a source of vanadate and a source of chromium; and a second supplement comprising Gymnema sylvestre and lipoic acid.

2. The nutritional system of claim 1, wherein the source of vanadate is vanadyl sulfate.

3. The nutritional system of claim 1, wherein the source of chromium is selected from the group consisting of chromium picolinate, chromium glucose tolerance factor, and mixtures thereof.

4. The nutritional system of claim 3, wherein the source of chromium comprises chromium picolinate and chromium glucose tolerance factor.

5. The nutritional system of claim 1, wherein the first supplement further comprises L-carnitine.

6. The nutritional system of claim 1, wherein the Gymnema sylvestre is provided as an extract from Gymnema sylvestre leaves.

7. A method of administering nutritional supplements, comprised of:
    (a) administering a first supplement comprising a source of vanadate; and then
    (b) administering a second supplement comprising an ingredient selected from gymnema sylvestre, lipoic acid or combinations thereof.

8. The method of claim 7, further comprising:
    (c) repeating steps (a) and (b).

9. The method of claim 7, wherein the first nutritional supplement further comprises a source of chromium.

10. The method of claim 7, wherein the first nutritional supplement comprises Gymnema sylvestre and lipoic acid, and the second nutritional supplement comprises a source of vanadate and a source of chromium.

11. The method of claim 7, wherein the first supplement is administered over a first time period, the second supplement is administered over a second time period, and the first and second time periods are different.

12. The method of claim 11, wherein the first and second time periods are between about 2 and about 6 months.

13. The method of claim 11, wherein the first supplement is administered over a first time period, the second supplement is administered over a second time period, and the first and second time periods are about 3 months.

14. The method of claim 13, wherein the first and second time periods are 90 days.

15. A nutritional system for improving glucose metabolism, comprising:
    a first supplement comprising a source of vanadate; and
    a second supplement comprising an ingredient selected from the group consisting of gymnema sylvestre, lipoic acid and combinations thereof.

16. The nutritional system of claim 15, wherein the first supplement further comprises a source of chromium.

17. A method of administering nutritional supplements, comprised of:
    (a) administering a first supplement comprising an ingredient selected from gymnema sylvestre, lipoic acid and combinations thereof; and then
    (b) administering a second supplement comprising a source of vanadate.

18. The method of claim 17, further comprising:
    (c) repeating steps (a) and (b).

19. The method of claim 17, wherein the second nutritional supplement further comprises a source of chromium.

20. The method of claim 17, wherein the first supplement is administered over a first time period, the second supplement is administered over a second time period that is different than the first time period.

21. The method of claim 17, wherein the first supplement is administered over a first time period, the second supplement is administered over a second time period, and the first and second time periods are between about 2 and about 6 months.

22. The method of claim 17, wherein the first supplement is administered over a first time period, the second supplement is administered over a second time period, and the first and second time periods are about 3 months.

23. The method of claim 22, wherein the first and second time periods are 90 days.

24. A nutrition supplement for improving glucose metabolism, comprising:
    (a) gymnema sylvestre; and
    (b) lipoic acid.

* * * * *

UNITED STATES PATENT AND TRADEMARK OFFICE
CERTIFICATE OF CORRECTION

PATENT NO. : 5,730,988
DATED : March 24, 1998
INVENTOR(S) : Rick W. Womack

It is certified that error appears in the above-indentified patent and that said Letters Patent is hereby corrected as shown below:

Cover page, please delete "Assignee: Lynntech, Inc., College Station, Texas."

Signed and Sealed this

FourthDay of August, 1998

Attest:

BRUCE LEHMAN

Attesting Officer

Commissioner of Patents and Trademarks